United States Patent [19]
Elphick et al.

[11] Patent Number: 5,386,835
[45] Date of Patent: Feb. 7, 1995

[54] BARRIER MEANS

[76] Inventors: Kevin J. Elphick, 96 Mullaloo Drive, Kallaroo, Western Australia 6025; Ilene F. Watters, 1/197 Walter Road, Dianella, Western Australia 6062, both of Australia

[21] Appl. No.: 873,825

[22] Filed: Apr. 27, 1992

Related U.S. Application Data

[63] Continuation-in-part of Ser. No. 490,670, Mar. 30, 1990, Pat. No. 5,152,282.

[51] Int. Cl.⁶ .......................... A61F 5/37; A61B 19/00
[52] U.S. Cl. .......................... 128/846; 128/849
[58] Field of Search .......................... 128/849–856, 128/846; 602/1, 3, 6, 41, 20, 23, 55, 60, 61

[56] References Cited

U.S. PATENT DOCUMENTS

| | | |
|---|---|---|
| 2,911,974 | 11/1959 | Spence . |
| 3,329,143 | 7/1967 | Gordon .................. 602/3 |
| 3,457,919 | 7/1969 | Harbard ................. 602/55 |
| 3,824,998 | 7/1974 | Snyder . |
| 3,921,627 | 11/1975 | Wilson ................... 128/853 |
| 4,178,924 | 12/1979 | Baxter .................... 602/3 |
| 4,224,935 | 9/1980 | Metelnick ............... 602/3 |
| 4,275,719 | 6/1981 | Mayer .................... 128/849 |
| 4,363,317 | 12/1982 | Broucek ................. 602/3 |
| 4,523,586 | 6/1985 | Couri ..................... 602/3 |
| 4,570,627 | 2/1986 | MacConkey et al. ... 128/849 |
| 4,727,864 | 3/1988 | Wiesenthal et al. ..... 602/3 |
| 4,966,135 | 10/1990 | Renfrew ................. 602/3 |
| 5,083,557 | 1/1992 | Lennon .................. 602/3 |

FOREIGN PATENT DOCUMENTS

| | | |
|---|---|---|
| 4906985 | 6/1986 | Australia . |
| WO8501439 | 4/1985 | WIPO . |
| WO8707137 | 12/1987 | WIPO . |

*Primary Examiner*—Michael A. Brown
*Attorney, Agent, or Firm*—Stevens, Davis, Miller & Mosher

[57] ABSTRACT

A barrier means (2) for connection to a body part to prevent wetting of the body part when liquid is externally applied to or near the body part comprising a web (4) formed of flexible and liquid impervious material and a strip (6) of liquid impervious adhesive extending about the periphery (8) on one side (10) of the web (4) for connecting and sealing the periphery (8) to the body part. The web (4) is dimensioned and shaped so that the surface area of one side (10) of the web (4) is greater than the area of the footprint of the web. This can be achieved by providing corrugations (12), pleats (20), folds (22), or a receptacle (24) in the web (4). Because the surface area of side (10) is greater than that of the footprint of the web, slack is formed in the web. The provision of this slack reduces the magnitude of tensile forces created in the web in response to movement of the body part and adjacent body parts to a level below that required to pull the periphery (8) away from the body. This ensures that a seal about the web (4) is always maintained thereby preventing the body part from becoming wet on the external application of liquid, for example, when bathing or showering.

21 Claims, 3 Drawing Sheets

BARRIER MEANS

This is a continuation-in-part of co-pending application Ser. No. 490,670, filed Mar. 30, 1990, and now U.S. Pat. No. 5,152,282.

In the Applicant's co-pending application, there is described an improved barrier means connectable to a part of a person's body to prevent that part from becoming wet during, for example, bathing or showering. One embodiment of the barrier means is in the form of a web of flexible and liquid impervious material having a liquid impervious strip extending around the periphery of the web with the strip having an adhesive backing for connecting the web to the body part. By manipulation of the strip, a receptacle can be formed in the web when applied to the body. The receptacle can accommodate a dressing attached to the body and provides a region of slack within the web which allows for body movement without pulling the strip away from the body part.

SUMMARY OF THE INVENTION

The Applicant has realized further embodiments of the web which are dimensioned and shaped to provide slack in the web so that when the web is connected to a body part it allows movement of the body part and adjacent body areas without pulling the web away from the body part. This ensures that a seal is maintained about the periphery of the web to prevent the body part from becoming wet when liquid is externally applied to or near the body part.

According to the present invention there is provided a barrier means for connection to a body part to prevent the body part from becoming wet when liquid is externally applied to or near the body part, the barrier means comprising:

- a web formed of flexible and liquid impervious material;
- a strip of liquid impervious adhesive extending about the periphery on one surface or side of the web for connecting and sealing the periphery of the web to the body part;
- the web being dimensioned and shaped so that the surface area of said one surface or side of the web is greater than the area of the footprint of the web thereby providing slack in the web when the web is connected and sealed to the body part,
- whereby the slack reduces the magnitude of tensile forces created in the web in response to movement of the body part and adjacent body areas to a level below that necessary to pull the periphery of the web away from the body part.

Preferably the web is provided with one or more corrugations extending between respective first and second spaced apart points located on the web.

Advantageously, at least one of said first and second points are located inboard of the strip.

In an alternative embodiment, the web is provided with one or more pleats, each pleat extending between respective first and second spaced apart points located on the web.

Preferably at least one of said first and second points is located inboard of the strip.

In one form of this embodiment, the pleats are formed by contacting portions of the strip onto itself about the periphery of the web.

In an alternative embodiment, the web is provided with a receptacle which opens onto said one side of the web, and is formed inboard of the strip of the web.

In one form of this embodiment, the receptacle is formed by non-elastically stretching a portion of the web inboard of the strip.

In another form of this embodiment, the receptacle is formed by cutting a hole in the web and attaching a pocket made of liquid impervious material and connecting an open end of the pocket over the hole in a leak-proof manner.

In an alternative embodiment, the slack in the web is provided by non-elastically stretching a portion of the web inboard of the strip.

In another embodiment, the web or at least the periphery of the web is made of a heat shrinkable, flexible and liquid impervious material wherein heat is applied to the periphery of the web thereby reducing the length of the periphery of the web and consequently providing a region of slack inboard of the periphery of the web.

Preferably the web further comprises a strip of release material releasably attached to the strip for protecting the strip prior to connecting the web to the body part, the strip of release material including a tab not attached to the strip to allow the strip of release material to be easily gripped and subsequently removed from the strip.

Preferably the strip of release material is divided into a number of lengths, where a first end of a first length underlies a first end of a second length, so that a first part of the first end of the second length is attached to the strip and a second part of the first end of the second length overlies the first end of the first length to form the tab.

Advantageously, the second length of release material is also provided with indicating means to direct a user of the web to initially remove the second length of release material when using the web.

Advantageously, the indicating means includes directions or instructions on how to apply the barrier means.

BRIEF DESCRIPTION OF THE DRAWINGS

Embodiments of the barrier means will now be described by way of example only, with reference to the accompanying drawings in which.

In the accompanying drawings like reference numbers denote like features.

DETAILED DESCRIPTION

Figure 1:
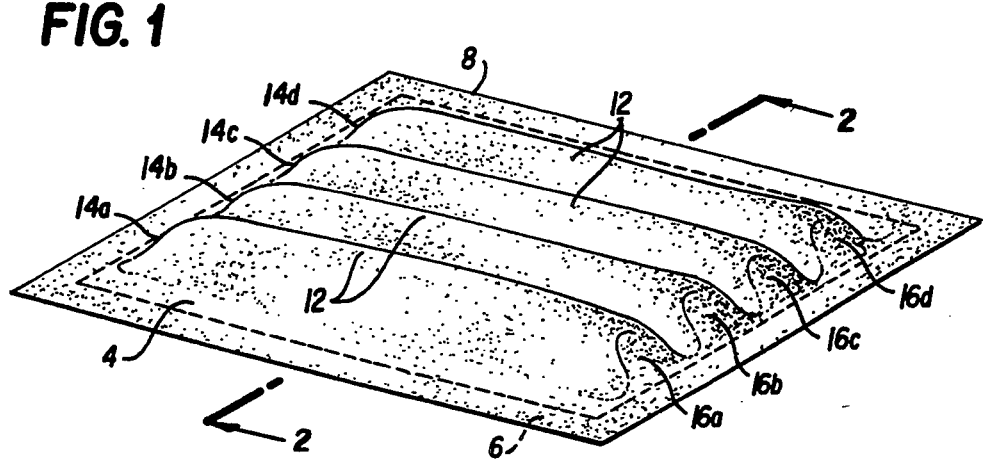
FIG. 1 is a perspective drawing of one embodiment of the web.
Figure 2:
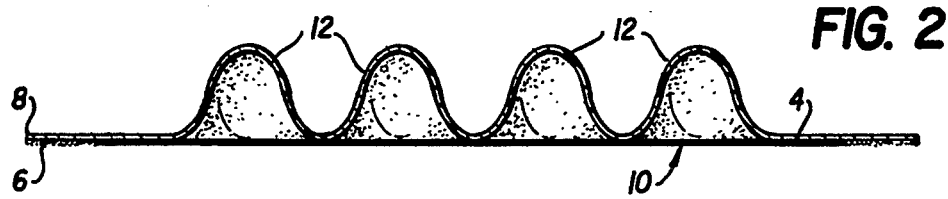
FIG. 2 is a view along section 2—2 of FIG. 1.

Referring to FIG. 1, there is illustrated a first embodiment of the barrier means 2 for connection to a body part to prevent wetting of the body part when liquid is externally applied to or near the body part comprises a web 4 made of flexible and liquid impervious material such as polyvinyl chloride (P.V.C). E.V.A. can also be added to the material of the web. A strip of liquid impervious adhesive 6 extends about the periphery 8 on one side 10 of the web 4 for connecting and sealing the periphery 8 to the body part. The web 4 is dimensioned and shaped so that the surface area of side 10 of the web 4 is greater than the area of the footprint of the web. Throughout this specification, the expression "area of the footprint of the web" is intended to mean the area covered by the web 4 when placed on a substantially planar surface. In other words, the area of the footprint is merely that bound by the periphery 8 of the web. For webs of regular geometric shape, the area of the footprint can be obtained using standard mathematical formulae. For example, for a square or rectangular web, the area of the footprint is merely the length times the breadth of the web. For a triangular shaped web, the area of the footprint is one half times the base times the height of the web and for a circular web, the area of the footprint is $\pi r^2$. In the embodiment in FIG. 1, the surface area of side 10 of the web 4 is formed to be greater than that of the footprint by formation of a plurality of corrugations 12 extending between respective first and second points $14_i$, $16_i$ (where i equals a to d). The points $14_i$, $16_i$ are located inboard of the periphery 8.

Because the surface area of side 10 is greater than that of the footprint of the web, slack is formed in the web. The provision of this slack reduces the magnitude of tensile forces created in the web 4 in response to movement of the body part and adjacent body parts to a level below that required to pull the periphery 8 away from the body part. This ensures that a seal about the web 4 is always maintained thereby preventing the body part from becoming wet on the external application of liquid, for example, when bathing or showering.

A further beneficial effect of creating slack in the web is that if a dressing is applied over a wound on the body part, the slack in the web 4 can readily accommodate the dressing without causing the web 4 to be become taut thus creating or facilitating the propagation of tensile forces within the web. This ensures that the beneficial effects of the slack are maintained not withstanding that the web also covers a dressing.

The amount of slack in the web can be increased by making the length of the corrugations 12 greater than the distance between corresponding first and second points $14_i$, $16_i$. This can most readily be achieved by non-elastically stretching the corrugations 12 in a lengthwise direction.

Figure 3:
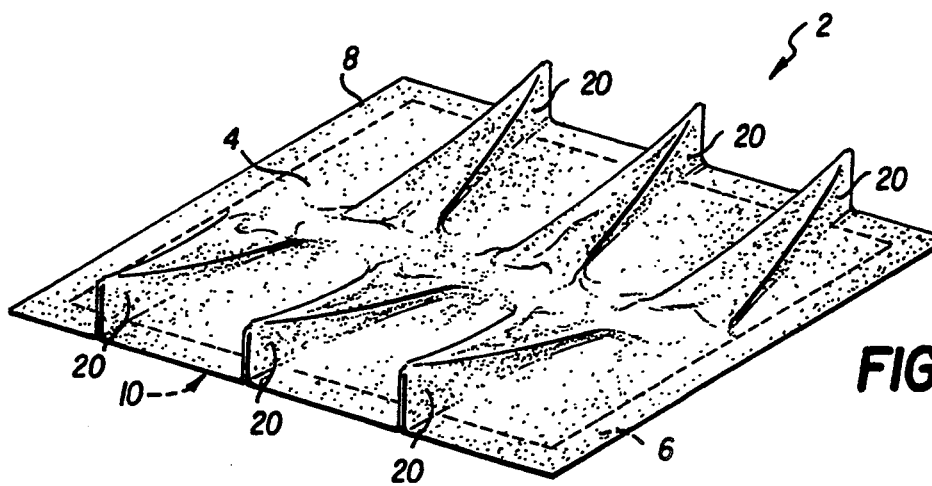
FIG. 3 is a perspective view of a second embodiment of the web.
Figure 4:
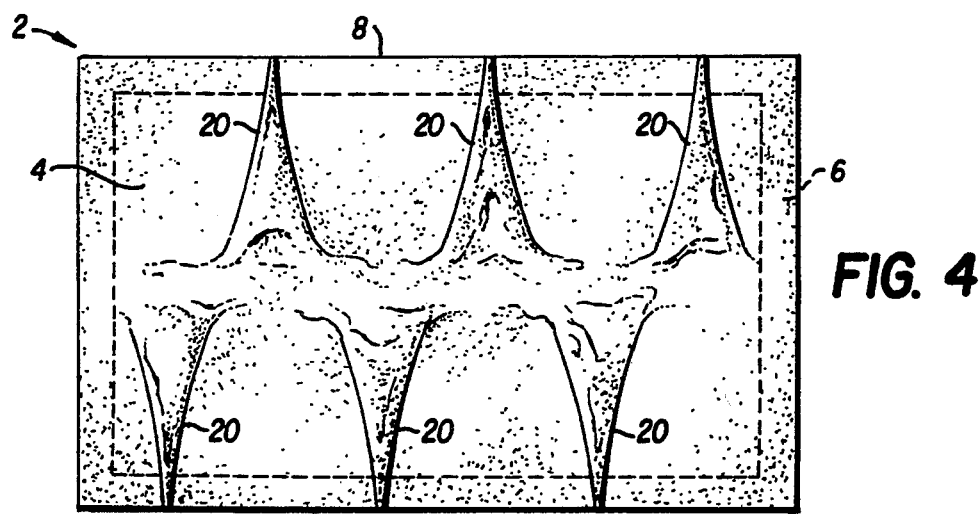
FIG. 4 is a plan view of the web shown in FIG. 3.

In the embodiment illustrated in FIGS. 3 and 4, the surface area of surface or side 10 of the web 4 is caused to be greater than that of the footprint of the web 4 by formation of a plurality of pleats 20 extending from the periphery 8 toward the centre of the web 4. The pleats 20 can be formed by gathering lengths of the periphery 8 and heat welding the gathered portions. The adhesive strip 6 can then be applied about the periphery 8 on side 10 of the web. The formation of the pleats 20 again results in slack being formed within the web 4 so as to allow for movement of the body part to which the web 4 is connected without the creation of tensile forces of a magnitude sufficient to pull the periphery 8 away from the body part.

Although in FIG. 3, the pleats 20 are shown as extending across the periphery 8, they may alternatively extend from a point inboard of the periphery 8 toward the centre of the web 4.

Figure 5:
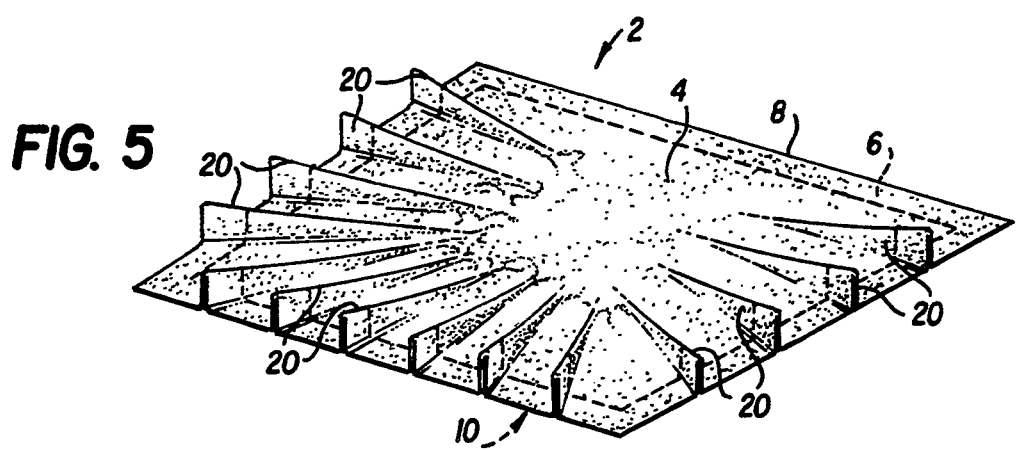
FIG. 5 is a perspective view of a third embodiment of the web.

In a variation of the embodiment shown in FIGS. 3 and 4, the pleats 20 can be formed by first applying the strip of adhesive 6 to the periphery 8 and then contacting lengths of the periphery 8 together, as illustrated in FIG. 5. In the embodiment shown in FIG. 5, it is of course not possible to form the pleats 20 inboard of the periphery 8 as there is nothing to hold gathered sections of the web together.

Figure 6:
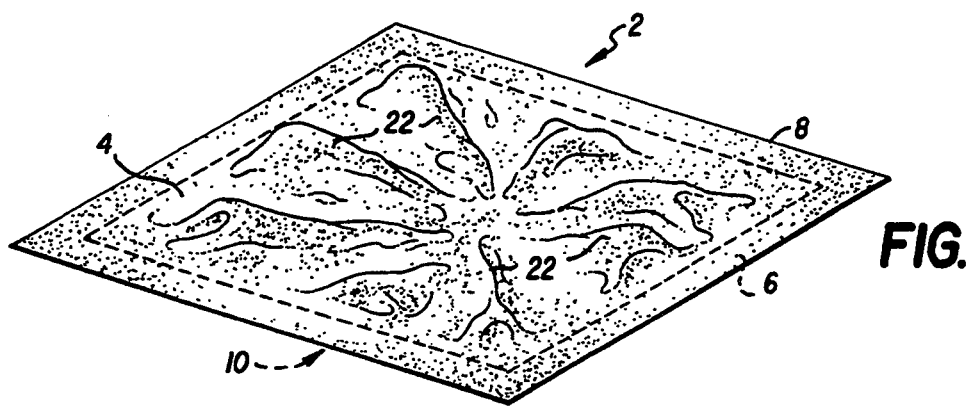
FIG. 6 is a perspective view of a fourth embodiment of the web.

In the embodiment illustrated in FIG. 6, the area of side 10 of the web is formed to be greater than that of the footprint by non-elastically stretching a portion of the web inboard of the periphery 8. The non-elastic stretching creates a plurality of loose folds 22 in the web 4. The loose folds 22 provide slack in the web 4 to reduce the magnitude of tensile forces created in the web in response to movement of a body part and adjacent body areas to a level below that necessary to pull the periphery 8 away from the body part. As with the above described embodiments, the loose folds 22 also allow the web to cover a dressing applied to the body part and maintain the aforementioned beneficial effects.

Figure 7:
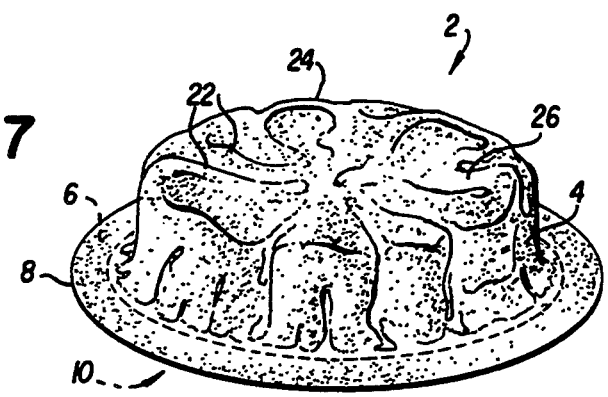
FIG. 7 is a perspective view of a fifth embodiment of the web.

In the embodiment illustrated in FIG. 7, the web 4 is approximately circular in shape and provided with a receptacle 24 which opens onto side 10 of the web and is formed inboard of the strip 6. The receptacle 24 can most easily be formed by non-elastically stretching a portion of the web 4 inboard of the strip 6. Alternatively, the receptacle can be formed by cutting a hole in the web 4 and attaching a pocket made of a liquid impervious material to the hole so that an open end of the pocket is connected in a leak-proof manner over the hole. In a further alternative, the receptacle can be formed by making the web or at least the periphery of the web of heat shrinkable material and then applying heat to the periphery. This will shrink the periphery thereby forming the receptacle.

The degree of slack provided in the web by the receptacle 24 can also be further increased by providing a plurality of loose folds 22 in an upper wall 26 of the receptacle 24 in a similar manner to that described with reference to the embodiment in FIG. 6.

Figure 8:
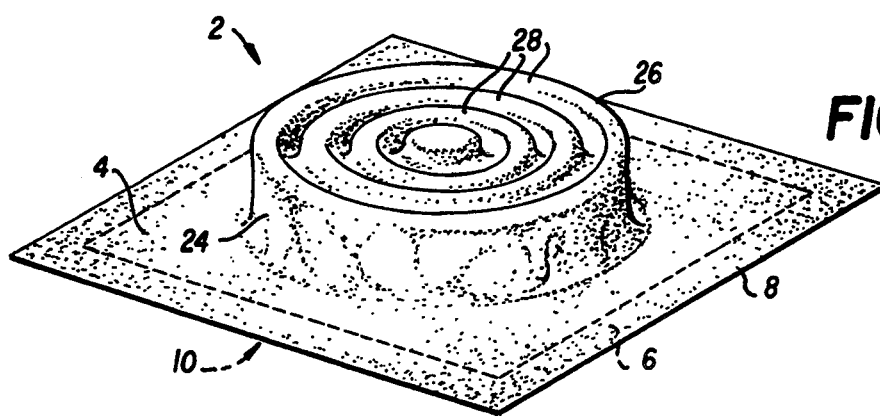
FIG. 8 is a perspective view of a sixth embodiment of the web.

FIG. 8 illustrates a variation of the receptacle 24 shown in FIG. 7. In the embodiment of FIG. 8, the receptacle 24 is formed with a plurality of substantially concentric corrugations 28. The corrugations 28 allow upper wall 26 of the receptacle 24 to expand in a concertina like manner. This further enhances the ability of the web 4 to receive relatively large dressings and still provide slack in the web in order to ensure that the periphery 8 does not pull away from the body part in response to movement of the body part of adjacent body areas. The circumference of each corrugation can be formed to be greater than $2\pi r$, where r is the radius of that corrugation, to provide even greater slack in the web 4.

Figure 9:
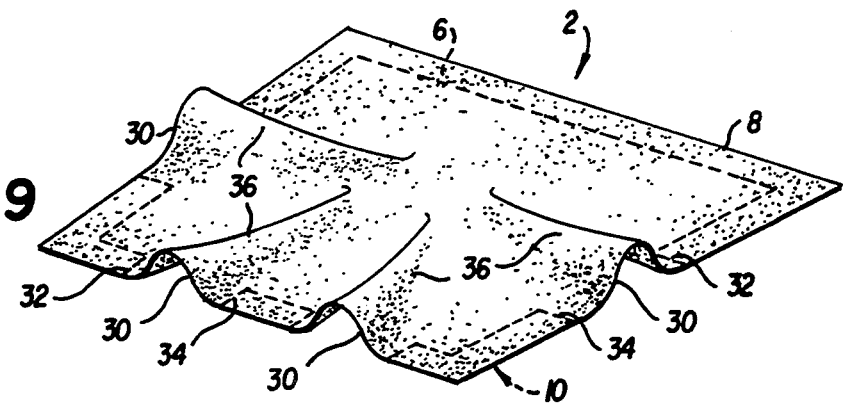
FIG. 9 is a perspective view of a seventh embodiment of the web.

FIG. 9 illustrates a further embodiment of the web 4 in which the adhesive strip 6 is discontinuous about the periphery 8. That is, there exists length 30 about the periphery 8 free of adhesive. Each length 30 is bound by edges 32 and 34. Web 4 is applied to the body by adhering the strip 6 in such a manner so that edges 32 and 34 of a length 30 are closer together than their distance apart when the web 4 is laid flat, i.e. their distance apart is decreased, for example the edges 32, 34 may be contacted onto a body part so that they are immediately adjacent to each other or overlap. This creates folds or corrugations 36 in the web 4 so as to provide slack to allow movement of the body part and adjacent areas without pulling the periphery 8 away from the body part. In the case where the edges 32, 34 are not adjacent, it is important that the corresponding length 30 be downstream of any liquid flow to prevent ingress of the liquid.

In all of the above embodiments, the web and/or periphery can be made of resilient material which is also flexible and liquid impervious.

Figure 10:
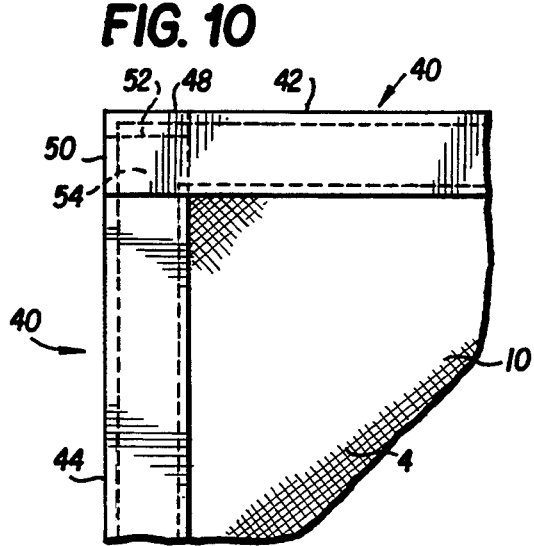
FIGS. 10 and 11 illustrate an arrangement of release material applicable to the web.
Figure 11:
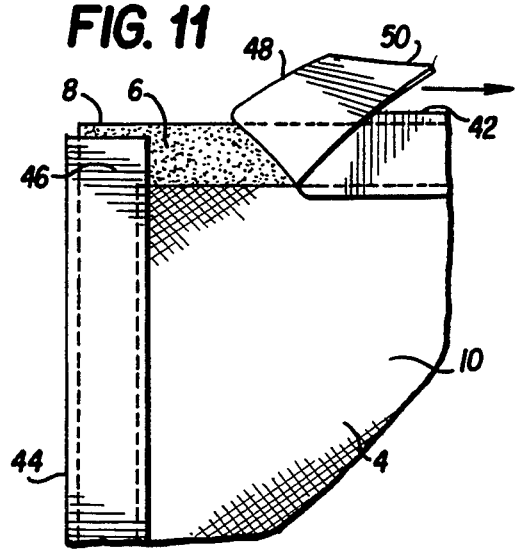

FIGS. 10 and 11 illustrate how release material in the form of release paper 40 is attached to the strip 6 for protecting the strip prior to connecting the web 4 to a body part. The release paper 40 is shown in two separate lengths 42 and 44. An end 46 of strip 44 underlies an end 48 of the strip 42. The portion of the end 48 which overlies the end 46 forms a tab 50 which is not adhered to the strip 6 and allows easy gripping of the release paper strip 42 to facilitate removal from the strip 6. In order to prevent end 48 of release paper strip 42 from fraying or becoming "dog eared" the end 46 of release paper strip 44 does not completely underlie end 48. Accordingly, a first part 52 of end 48 directly contacts the strip 6 and is therefore adhered to the periphery 8. A second part 54 of the end 48 which overlies end 46 forms the tab 50.

It is sometimes important that one edge of the web 4 be initially contacted and sealed to a body part. By formation of tab 50 a user is directed to remove the strip 42 initially. This is because the tab 50 makes it easier to remove the strip 42 than any other strip. Accordingly, the provision of the tab 50 greatly assists in the correct use and application of the web 4. Indicating means such as visible marks or printed instructions can also be applied to the first strip 42 directing the user to initially remove that strip when applying the web 4, assuming that it is preferable to have strip 42 removed first, in order to ensure correct application of the web 4. After removal of the strip 42 adjacent strip 44 can be peeled off, as can another strip of release paper (not shown) adjacent an end of strip 42 opposite end 48. The configuration of the first and second strips 42, 44 directs a user to initially remove the first strip 42 (i.e. the top strip) when applying the web.

In an alternate embodiment, the ends 46 and 48 can be dimensioned so as to abut each other and fully cover the adhesive strip 6. A tab can then be attached to one of the strips 42, 44 in any conventional manner (e.g. by use of adhesive to facilitate removal of that particular strip). Although the release paper 40 is shown as being formed from a plurality of lengths 42, 44, it can of course be formed from a single continuous strip with one or more tabs attached thereto in conventional manner.

It will be apparent from the above-described embodiments that a barrier means in accordance with the present invention has significant advantages over simple flat planar webs. In the present invention, the webs are formed with a surface area on one side greater than the footprint of the web. This causes slack in the web which in turn allows movement of a body part onto which the web is applied without the transmission or creation of tensile forces of sufficient magnitude to pull the web away from the body part covered by the web. Thus, the body part is always maintained in a dry state. Significantly, it allows the person to which the web 4 is applied, freedom to move in a normal and comfortable manner and allow that person to wash and bath without fear of the web becoming detaching and the body part becoming wet. The slack in the web also allows for the web to cover a dressing applied to the body part while maintaining the above beneficial effects.

Modifications and variations such as would be apparent to persons of ordinary skill in the relevant arts are deemed to be within the scope of the present invention.

The claims defining the invention are as follows:

1. A barrier means for connection to a body part to prevent the body part from becoming wet when liquid is externally applied to or near the body part, the barrier means comprising:

a web formed of flexible and liquid impervious material and having two surfaces and a periphery;

a strip of liquid impervious adhesive extending about the periphery on one surface of the web for connecting and sealing the periphery of the web to the body part;

the web being dimensioned and shaped so that the area of said one surface of the web is greater than the area of the footprint of the web thereby providing slack in the web when the web is connected and sealed to the body part, whereby the slack reduces the magnitude of tensile forces created in the web in response to movement of the body part and adjacent body areas to a level below that necessary to pull the periphery of the web away from the body part.

2. A barrier means according to claim 1, wherein the web is provided with one or more corrugations extending between respective first and second spaced apart points located on the web.

3. A barrier means according to claim 2, wherein the length of each corrugation is greater than the distance between respective first and second points.

4. A barrier means according to claim 3, wherein at least one of the first and second points are located inboard of the adhesive strip.

5. A barrier means according to claim 1, wherein the web is provided with one or more pleats, each pleat ending between respective first and second spaced apart points located on the web.

6. A barrier means according to claim 5, wherein at least one of said first and second points is located inboard of the adhesive strip.

7. A barrier means according to claim 5, wherein the pleats are formed by contacting portions of the adhesive strip onto itself about the periphery of the web.

8. A barrier means according to claim 1, wherein the web is provided with a receptacle which opens onto said one surface of the web and is formed inboard of the adhesive strip of the web.

9. A barrier means according to claim 8, wherein the receptacle is formed by non-elastically stretching a portion of the web inboard of the adhesive strip.

10. A barrier means according to claim 8, wherein the receptacle is formed by cutting a hole in the web and attaching a pocket made of liquid impervious material to the hole by connecting an open end of the pocket over the hole in a liquid proof manner.

11. A barrier means according to claim 8, wherein the receptacle includes an upper wall provided with a plurality of concentric corrugations so that the upper wall can expand in a concertina like manner.

12. A barrier means according to claim 11, wherein the circumference of each corrugations is greater than 2πr, where r is the radius of respective corrugations.

13. A barrier means according to claim 8, wherein the receptacle includes an upper wall which is non-elastically stretched to form one or more folds.

14. A barrier means according to claim 1, wherein at least the periphery of the web is made of a heat shrinkable, flexible and liquid impervious material wherein, heat is applied to the periphery of the web thereby reducing the length of the periphery of the web and consequently providing a region of slack inboard of the periphery of the web.

15. A barrier means according to claim 1, further comprising a strip of release material releasably attached to the adhesive strip for protecting the adhesive strip prior to connecting the web to the body part, the strip of release material including a tab not attached to the adhesive strip to allow the strip of release material to be easily gripped and subsequently removed from the adhesive strip.

16. A barrier means according to claim 15, wherein the strip of release material is divided into a number of lengths, where a first end of a first length underlies a first end of the second length in a manner so that a first part of the first end of the second length is attached to the adhesive strip and the second part of the first end of the second length overlies the first end of the first length to form the tab.

17. A barrier means according to claim 16, wherein the second length of release material is also provided with indicating means to direct a user of the web to initially remove the second length of release material when using the web.

18. A barrier means according to claim 17 wherein the indicating means includes directions or instructions on how to apply the barrier means.

19. A barrier means according to claim 1 wherein the periphery is made of a resilient material.

20. A barrier means according to claim 1 wherein the web is made of a resilient material.

21. A barrier means for connection to a body part to prevent the body part from becoming wet when liquid is externally applied to or near the body part, the barrier means comprising:

a web formed of flexible and liquid impervious material;

a strip of liquid impervious adhesive extending about the periphery on one side of the web for connecting and sealing of the periphery of the web to the body part, the adhesive strip having at least one discontinuity bound by respective opposite edges, so that when the web is connected to the body part by contacting the adhesive strip in such a manner that the distance between the respective opposite edges is decreased thereby creating a corrugation in the web, the surface area of the web as applied is greater than that of the footprint of the web as applied, thereby providing slack in the web when the web is connected and sealed to the body part, whereby the slack reduces the magnitude of tensile forces created in the web in response to movement of the body part and adjacent body areas to a level below that necessary to pull the periphery of the web away from the body part.

* * * * *